(12) United States Patent
Reardon

(10) Patent No.: US 8,012,458 B2
(45) Date of Patent: Sep. 6, 2011

(54) RARE-EARTH AMIDATE COORDINATION COMPOUNDS

(75) Inventor: Damien F. Reardon, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1124 days.

(21) Appl. No.: 11/759,973

(22) Filed: Jun. 8, 2007

(65) Prior Publication Data

US 2008/0306251 A1    Dec. 11, 2008

(51) Int. Cl.
*A61B 5/055*       (2006.01)
*G01N 33/20*     (2006.01)

(52) U.S. Cl. .................. 424/9.36; 424/9.3; 424/9.361; 436/82

(58) Field of Classification Search ............... 424/9.3, 424/9.36, 9.361; 436/82
See application file for complete search history.

(56) References Cited

U.S. PATENT DOCUMENTS

2004/0262575 A1   12/2004   Potrawa et al.
2005/0178841 A1    8/2005   Jones, II et al.

OTHER PUBLICATIONS

Yan, B., J. Fluoresc., 2007, 17, p. 155-161.*
Rizvi, S. et al., Bull. Chem. Soc. Ethiopia, 1992, 6(2), p. 115-118.*

* cited by examiner

*Primary Examiner* — Michael G Hartley
*Assistant Examiner* — Leah Schlientz

(57) ABSTRACT

The invention is directed to a lanthamide chelate composition having a lanthamide, a charged amidate ligand, and a mono- or bidentate neutrally charged coordination compound, the composition being represented by structure I or structure II

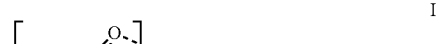

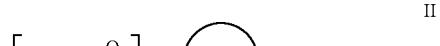

wherein $Ln^{3+}$ designates lanthamide, $R_1$ is alkyl, aryl, or heteroaryl; $R_2$ is alkyl, aminoalkyl, aryl or heteroaryl; M is a neutrally charged monodentate coordination compound, M' is a neutrally charged bidentate coordination compound, a=1 or 2; and wherein M and M' comprise N, S, or O. It extends to the process of making the composition.

10 Claims, 1 Drawing Sheet

RARE-EARTH AMIDATE COORDINATION COMPOUNDS

FIELD OF THE INVENTION

The present invention relates to luminescent coordination compounds formed from rare-earth amidate chelates. Potential uses include marking goods for purposes of identification.

BACKGROUND OF THE INVENTION

A wide variety of luminescent rare-earth-containing compositions are known in the art. Both inorganic and organometallic luminescent rare-earth-containing compositions have been identified.

Rare-earth metal ions absorb ultraviolet light and luminesce in the visible or the infrared. When a rare-earth is complexed with certain aryl organic ligands luminescence quantum yield of the rare-earth is enhanced by the broad band absorbance of the organic moiety in the ultraviolet spectrum which can efficiently transfer energy non-radiatively to the emitting rare-earth ion.

Mathur et al., Synth. React. Inorg. Met.-Org. Chem. 11(3), 231-244 (1981) discloses lanthamide chelates wherein the associated ligands are represented by the formula $R_1NHC(O)R_2$ wherein $R_1$ is phenyl, chloro-phenyl, or nitro-phenyl, and $R_2$ is methyl or phenyl with the proviso that when $R_2$ is phenyl, $R_1$ must also be unsubstituted phenyl. The lanthamide chelates disclosed therein were employed for infrared spectroscopic studies.

Many types of ligands are known in the art for use in forming chelates with rare-earth metals, and, even more generally, with transition metals. Despite this plethora of compositions, there is a continuing need for rare-earth chelates that luminesce with high quantum yield, particularly in the visible part of the spectrum, and that exhibit thermal stability for good processibility and extended use temperatures.

SUMMARY OF THE INVENTION

The present invention provides a composition comprising a lanthamide chelate comprising a lanthamide, a charged amidate ligand, and a mono- or bidentate neutrally charged coordination compound, the composition being represented by structure I or structure II

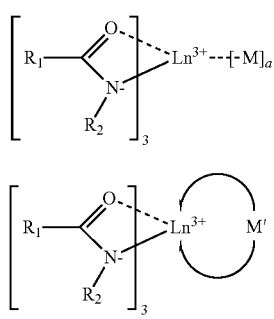

wherein $Ln^{3+}$ designates lanthamide, $R_1$ is alkyl, aryl, or heteroaryl; $R_2$ is alkyl, aminoalkyl, aryl or heteroaryl; M is a neutrally charged monodentate coordination compound, M' is a neutrally charged bidentate coordination compound, a=1 or 2; and wherein further M and M' comprise N, S, or O.

Further provided is a process comprising combining in an organic solvent a lanthamide ester and a compound represented by the formula

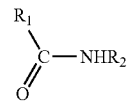

wherein $R_1$ is alkyl, aryl, or heteroaryl; $R_2$ is alkyl, aminoalkyl; aryl or heteroaryl; mixing the ingredients so combined for a length of time necessary to achieve the desired amount of a tris-amidato-lanthamide chelate represented by structure III wherein $Ln^{3+}$ designates lanthamide, $R_1$ is alkyl, aryl, or heteroaryl, substituted or unsubstituted; $R_2$ is alkyl, aminoalkyl, aryl or heteroaryl,

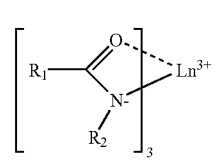

substituted or unsubstituted; and, addition of a neutrally charged coordinating ligand to a solution of the thus prepared tris-amidato-lanthamide chelate to prepare a lanthamide chelate represented by structure I or structure II.

DETAILED DESCRIPTION

Figure 1:
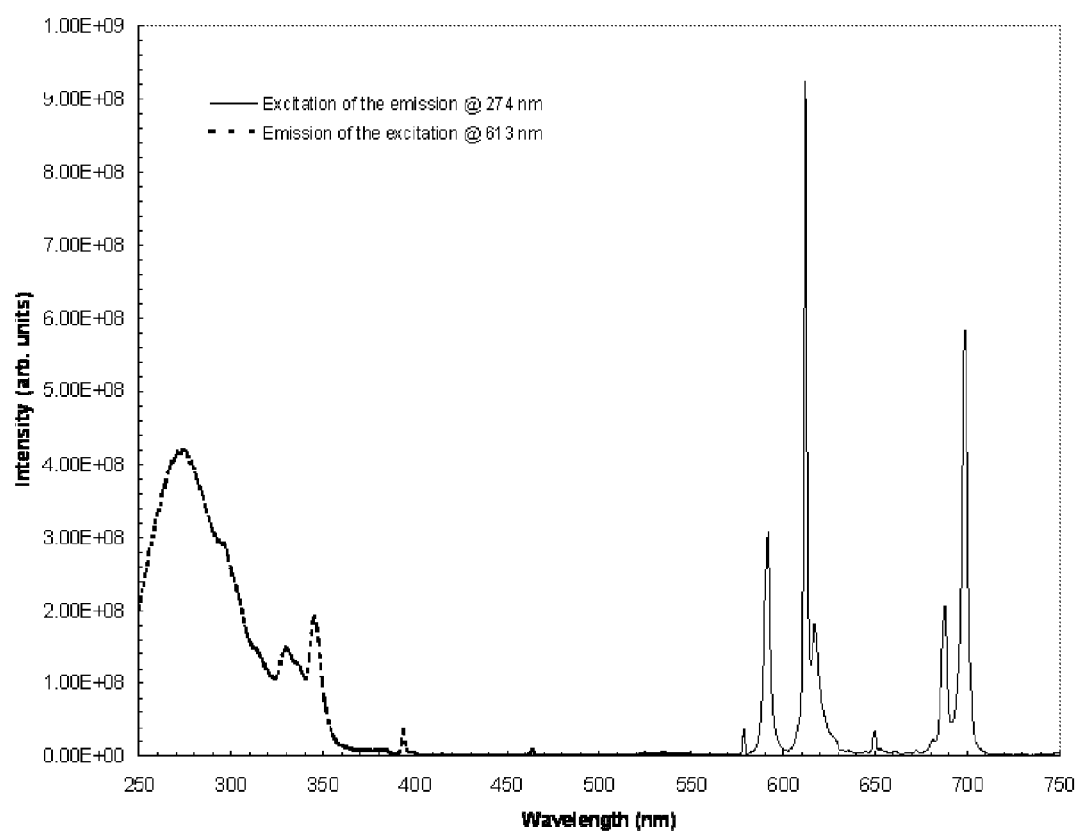
FIG. 1 illustrates the excitation and luminescence spectra of a product in powder form for corresponding Examples 1.

The term "ligand" as found herein refers to an organic amide compound that can bond to a lanthamide metal by overlap of an empty orbital on the metal with a filled orbital on the ligand. The bonded anionic ligand is called the amidate. The "amide" is the neutrally charged "protonated" ligand and the "amidate" is its "anionic" counterpart which

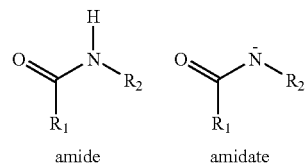

has been deprotonated and bears a delocalized negative charge through its resonance structure, as indicated by the structures:

The term "chelate" means an inorganic complex formed among a lanthamide metal, a charged ligand, and a neutrally charged monodentate or bidentate coordination compound, wherein the charged ligand has a plurality of binding sites and wherein the charged ligand is bound to the metal at two or more of the binding sites of the ligand, and wherein the neutrally charged monodentate or bidentate coordination compound comprises N, S, or O.

The present invention provides rare-earth amidate chelates that provide a desirable combination of luminescence and thermal stability. The compositions of the present invention are useful for formulating coating compositions, including inks, paints, suitable for use in applying coatings on the surface of articles. Examples of articles include cosmetic products, clothing, identification of genetic material (DNA), proteins. One particularly useful application is in the area of identifying marks, such as for product authentication. Because of their thermal stability, the compositions of the present invention are well-suited for use in melt blending with polymers using conventional plastics processing methods, and forming into luminescent films or other shaped articles.

The amide and amidate structures represented in the formulae (I), (II) and (III) are found in the art to be resonant structures, as indicated by the following equilibrium reactions:

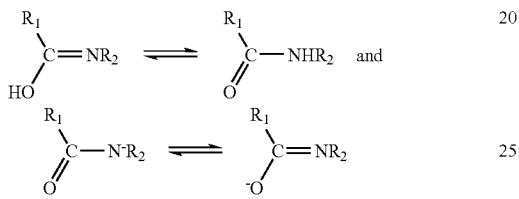

respectively. Throughout the present invention, formulae (I), (II) and (III) will be employed to represent both resonant structures of each composition referred to.

Any lanthamide except promethium and lutetium are satisfactory for use in the present invention. Preferred lanthamides are those that luminesce in the visible portion of the electromagnetic spectrum, including europium, dysprosium, samarium, terbium. Suitable lanthamides are in the +3 valence states. In one embodiment, the lanthamide is $Eu^{3+}$. In another embodiment the lanthamide is $Dy^{3+}$. In another embodiment the lanthamide is $Sm^{3+}$. In still another embodiment, the lanthamide is $Tb^{3+}$.

Suitable aryls include but are not limited to phenyl, napthyl, anthracyl, or phenanthrenyl. Suitable heteroaryls include but are not limited to pyridinyl, quinolinyl, thionyl, furanyl, pyrollyl, oxazollyl, imidazollyl, pyrimidinyl, purinyl, nucleosides or keto tautomers of their enol forms. All aromatic compositions described herein may be substitute or unsubstituted. Examples of substituents include but are not limited to the radicals such as alkyl, aryl, halo, alkoxy, halogenated alkyl, sulfanyl, secondary amino, or nitro.

Suitable aminoalkyl groups are represented by the formula

wherein each $R_3$ can independently be C1-C8 alkyl, preferably C1-C3, and $R_4$ can be C1-C8 alkenyl, preferably C2-C4. Most preferably, $R_3$ is methyl, and $R_4$ is ethenyl.

Amidate ligands suitable for the composition of the present invention include but are not limited to those represented by the formulae following, wherein Q can be O or S. Further, any six ring aryl structure can be replaced by a pyridinyl ring. Any of the aromatic rings can also have substituents including but not limited to alkyl, aryl, halo, alkoxy, halogenated alkyl, sulfanyl, secondary amino, or nitro.

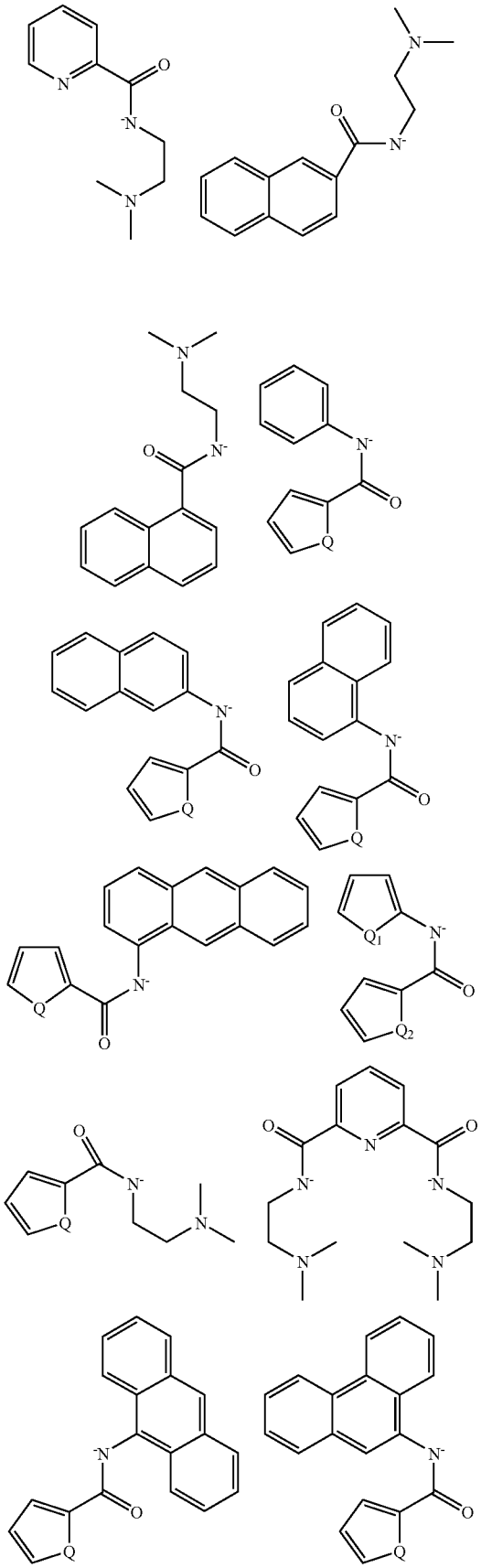

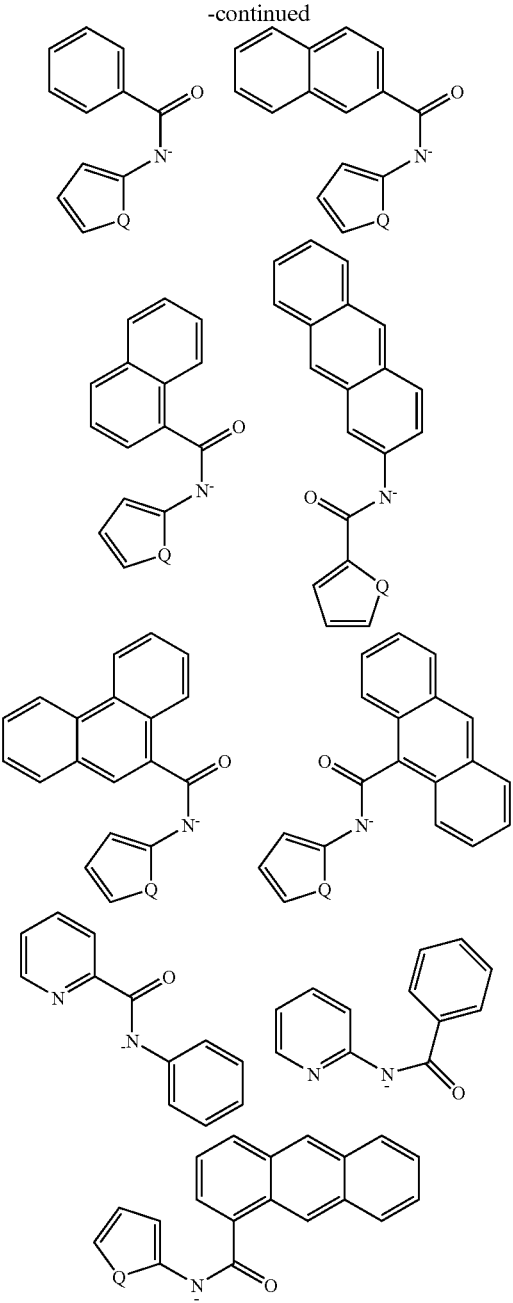

Also included are ligands having multiple heteroatoms in the aryl ring. For example pyrimidine, thiazole, oxazole, pyrrole, oxazole, imidazole, pyrimidine, purine, nucleosides or keto tautomers of their enol forms may be substituted for any of the aryl rings.

Embodiments of combinations of $R_1$ and $R_2$ in the anionic amidate ligand according to the present invention are recited in Table 1.

TABLE 1

| $R_1$ | $R_2$ |
|---|---|
| Heteroaryl ring | Aryl ring |
| Heteroaryl ring | Dialkylaminoalkyl group |
| Aryl ring | Dialkylaminoalkyl group |

TABLE 1-continued

| $R_1$ | $R_2$ |
|---|---|
| Aryl ring | Aryl ring |
| Aryl ring | Heteroaryl ring |

Examples of embodiments of the heteroaryl ring include thiophenyl, pyridinyl or furanyl. Examples of embodiments of the aryl ring include phenyl, naphthyl, anthracyl, or phenanthranyl. An embodiment of the dialkylaminoalkyl group is dialkylaminoethyl. An embodiment of the dialkylaminoethyl is dimethylaminoethyl.

The lanthamide amidate complexes recited above are in combination with neutrally charged monodentate or bidentate coordinating ligands as represented in the structure I or structure II

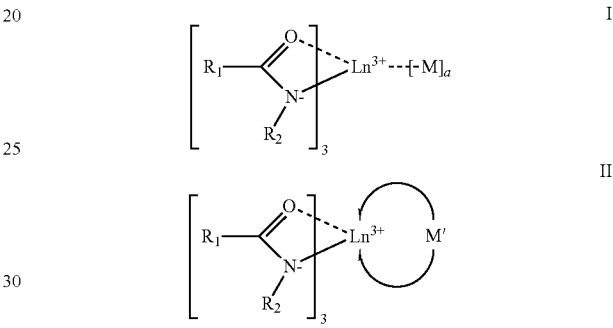

wherein $Ln^{3+}$ designates lanthamide, $R_1$ is alkyl, aryl, or heteroaryl; $R_2$ is alkyl, aminoalkyl, aryl or heteroaryl; M is a neutrally charged monodentate coordination compound, M' is a neutrally charged bidentate coordination compound, a=1 or 2; and wherein further M and M' comprise N, S, or O.

Suitable neutrally charged monodentate or bidentate ligands include but are not limited to heteroaryl rings, such as pyridine, pyridine-N-oxide, thiophene, furane, ketones, such as benzophenone, 1,10-phenathroline, tri-substituted phosphine oxides, such as tri-phenyl phosphine oxide, and 1,2-ethylenebis(diphenylphosphine oxide).

Coordinating neutrally charged ligands are represented in the following structures:

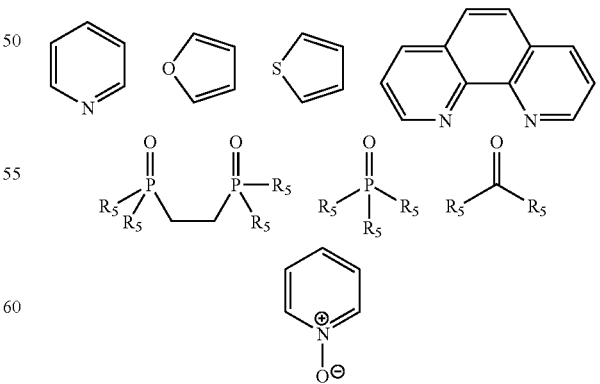

wherein each $R_5$ can independently be aryl or C1-C6 alkyl.

In first step of the process of the invention, a saturated aliphatic lanthamide carboxylate or fluorocarboxylate having one to eight carbons, preferably one to six carbons, most preferably one to three carbons, is combined in a solvent with a compound represented by the formula

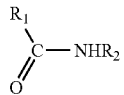

IV wherein $R_1$ is alkyl, aryl, or heteroaryl; and $R_2$ is alkyl, aminoalkyl; aryl or heteroaryl, and, the combination so prepared is mixed for a length of time necessary to achieve the desired amount of lanthamide amidate product (III).

A lanthamide fluorocarboxylate is preferred. More preferred is a lanthamide trifluoroacetate. Any lanthamide except promethium and lutetium are satisfactory for use in the process. Preferred lanthamides are those that luminesce in the visible portion of the electromagnetic spectrum, including europium, dysprosium, samarium, and terbium. The lanthamides suitable for use in the process hereof are in the +3 valence states such as $Eu(CF_3COO)_3$, $Dy(CF_3COO)_3$, $Sm(CF_3COO)_3$ and $Tb(CF_3COO)_3$. Suitable solvents are linear or cyclic alkanes, and aryl hydrocarbons, both halogenated and non-halogenated. An embodiment is dichloromethane.

Suitable aryls for use in $R_1$ or $R_2$ include but are not limited to phenyl, napthyl, anthracyl, or phenanthrenyl. Suitable heteroaryls include but are not limited to pyridinyl, quinolinyl, thionyl, furanyl, pyrollyl, oxazollyl, imidazollyl, pyrimidinyl, purinyl, nucleosides or keto tautomers of their enol forms. Suitable aryls or heteroaryls include substituted aryls or heteroaryls. Suitable substituents include but are not limited to the radicals such as alkyl, aryl, halo, alkoxy, halogenated alkyl, sulfanyl, secondary amino, or nitro.

Suitable aminoalkyl groups are represented by the formula

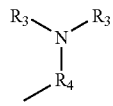

where each $R_3$ can independently be C1-C8 alkyl, preferably C1-C3, and $R_4$ can be C1-C8 alkenyl, preferably C2-C4. Most preferably, $R_3$ is methyl, and $R_4$ is ethenyl.

Suitable examples of compound (IV) include but are not limited to compounds of the following formulae, wherein Q can be O or S. Further, any six ring aryl structure can be replaced by a pyridinyl ring. Any of the aromatic rings can also have substituents including but not limited to alkyl, aryl, halo, alkoxy, halogenated alkyl, sulfanyl, secondary amino, or nitro.

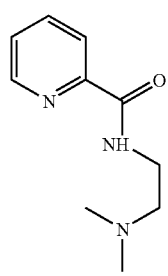

IVa

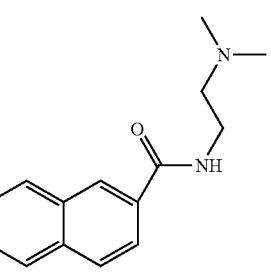

IVb

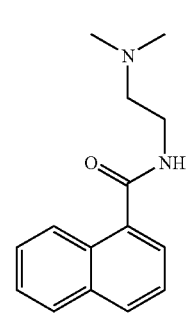

IVc

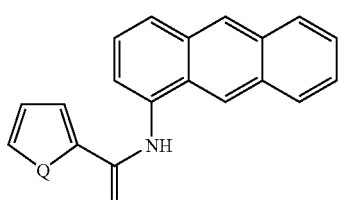

IVd

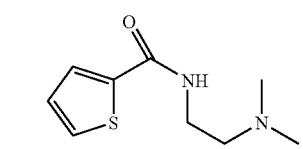

IVe

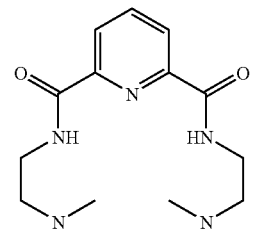

IVf

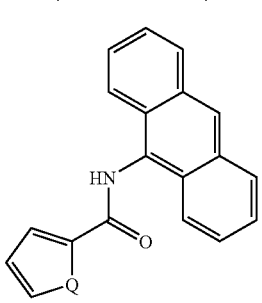

IVg

-continued

IVh

IVi

IVj

IVk

IVl

IVm

-continued

IVn

IVo

IVp

IVq

IVr

IVs

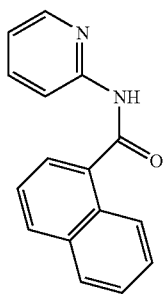

Also included are ligands having multiple heteroatoms in the aryl ring. For example pyrimidine, thiazole, oxazole, pyrrole, oxazole, imidazole, pyrimidine, purine, nucleosides or keto tautomers of their enol forms may be substituted for any of the aryl rings.

Embodiments of combinations of $R_1$ and $R_2$ in the anionic amide ligand according to the process are recited in Table 1. Any of the aromatic rings in the compositions of Table 1 can also have substituents including but not limited to alkyl, aryl, halo, alkoxy, halogenated alkyl, sulfanyl, secondary amino, or nitro.

Examples of embodiments of the heteroaryl ring include thiophenyl, pyridinyl or furanyl. Examples of embodiments of the aryl ring include phenyl, naphthyl, anthracyl, phenanthranyl. Preferably, the dialkylaminoethyl group is dimethylaminoethenyl.

Suitable compounds (IV) are known in the art, and can be prepared according to the methods of the art. For example, compound (III) where Q is sulfur can be prepared according to the method of Buu-Hoi et al., Recueil des Travaux Chimiques des Pays-Bas et de la Belgique (1949) 68, 5-33. Compound (IIs) can be prepared according to the method of Yabunouchi et al., WO2006073059. Compound (IIk) can be prepared according to the method of Beckmann et al., Berichte der Deutschen Chemischen Gesellschaft [Abteilung] B: (1923), 56B, 341-354. Compound (IIc) can be prepared according to the method of Giannini et al., Farmaco, Edizione Scientifica (1973), 28(6), 429-447. Compound (IIf) can be prepared according to the method of Davies et al., J. Organometallic Chem. (1998), 550(1-2), 29-57.

It has been found satisfactory in the process to react the reactants at room temperature. However, it is anticipated that higher temperatures will accelerate the reaction. In general the maximum temperature of reaction will be limited by the boiling point of a suitable solvent. In general, it is found satisfactory to combine reactants at concentrations in a 3:1 mole ratio of the amide ligand to the lanthamide starting precursor with the exception of ligand IIF where the reaction occurred in a 2:1 mole ratio of amide ligand to the lanthamide precursor.

The product produced in the first step of the process is a tris-amidato lanthamide chelate as represented by the structure (III)

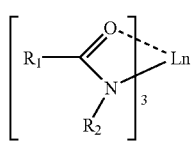

wherein Ln designates lanthamide, $R_1$ is alkyl, aryl, or heteroaryl; $R_2$ is alkyl, aminoalkyl, aryl or heteroaryl.

In a second step of the process according to the present invention a neutrally charged monodentate or bidentate coordinating ligand is added to a solution of the tris-amidato-lanthamide chelate (III) formed as described supra. Suitable neutrally charged monodentate or bidentate coordinating ligands include but are not limited to heteroaryl rings such as pyridine, thiophene, furane, ketones, preferably benzophenone, 1,10-phenathroline, tri-substituted phosphine oxides, preferably tri-phenyl phosphine oxide, and 1,2-ethylenebis(diphenylphosphine oxide) as represented in the following structures, which can have substituents including but not limited to alkyl, aryl, halo, alkoxy, halogenated alkyl, sulfanyl, secondary amino, or nitro:

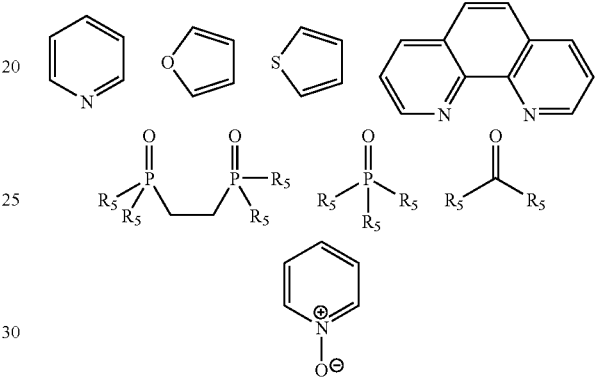

wherein each $R_5$ can independently be aryl or C1-C6 alkyl.

In one embodiment, coordination of a neutrally charged bidentate ligand to the tris amidato lanthamide in the mole ratio range of 1:1 will yield the structure V:

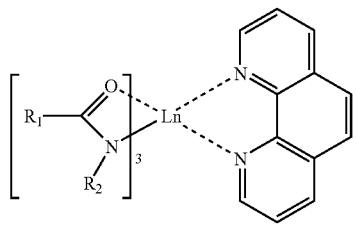

wherein Ln is a lanthamide, $R_1$ is alkyl, aryl, or heteroaryl; $R_2$ is alkyl, aminoalkyl; aryl or heteroaryl. Preferably Ln is $Eu^{3+}$, $Dy^{3+}$, $Sm^{3+}$, or $Tb^{3+}$.

In an alternative embodiment, coordination of a neutrally charged bidentate ligand to the tris amidato lanthamide in the mole ratio range of 1:1 will yield the structure VI

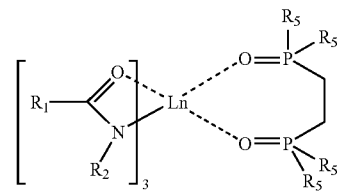

wherein Ln is a lanthamide, $R_1$ is alkyl, aryl, or heteroaryl; $R_2$ is alkyl, aminoalkyl; aryl or heteroaryl, and each $R_5$ can independently be aryl or C1-C6 alkyl. Embodiments of Ln may be selected from $Eu^{3+}$, $Dy^{3+}$, $Sm^{3+}$ or $Tb^{3+}$.

In another alternative embodiment coordination of a neutrally charged monodentate ligand to the tris amidato lanthamide in the mole ratio range of 1:2 will yield the structure VII

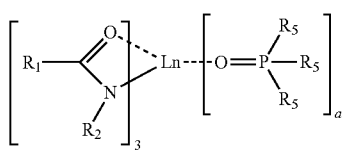

VII wherein a=2, Ln is a lanthamide, $R_1$ is alkyl, aryl, or heteroaryl, substituted or unsubstituted; $R_2$ is alkyl, aminoalkyl; aryl or heteroaryl, and each $R_5$ can independently be aryl or C1-C6 alkyl. Preferably Ln is $Eu^{3+}$, $Dy^{3+}$, $Sm^{3+}$, or $Tb^{3+}$.

Or, in yet another alternative embodiment coordination of a neutrally charged monodentate ligand to the tris amidato lanthamide in the mole ratio range of 1:1 will yield the structure VII wherein a=1.

The rare-earth-chelates hereof can be combined with other ingredients to form compositions suitable for use as coatings or inks. In one embodiment, the rare-earth-chelate hereof is incorporated into an ink composition suitable for printing. In one embodiment the rare-earth-chelate is placed into dichloromethane to form an ink suitable for printing. In another embodiment, the rare-earth-chelate is incorporated into a paint composition to form a composition suitable for paints, which can be applied by any method known in the art including by brushing, rolling, or spraying.

Numerous chemical formulations are known in the art for preparing inks, paints, and other coating compositions. Any composition in the art that contains inorganic pigments in particulate form can be employed to formulate an ink, paint, or other coating composition with the rare-earth-chelate hereof serving as the pigment. The rare-earth-chelate hereof may serve as the only pigment, or it may be combined with other pigments and particulate matter such as is known to be suitable for use in the art of inks and coatings. In any case, the resulting coating formed therefrom is luminescent upon exposure to ultraviolet light that corresponds to an excitation wavelength of the specific composition.

The composition hereof is particularly useful for use in an ink-jet printing ink employed for marking articles, particularly manufactured goods subject to counterfeiting.

The invention hereof is further described in the following specific embodiments, but is not limited thereto.

EXAMPLES

Luminescence Spectra

The luminescence spectra in the examples below were determined using a Jobin-Yvon Spex Fluorolog spectrofluorometer. A 450 W Xe lamp was used as the excitation source. Gratings blazed at 330 nm with 1200 grooves/mm were used in the excitation monochromator. Gratings blazed at 500 nm with 1200 grooves/mm were used in the emission monochromator. A dry powder sample was loaded into a 15 mm long by 5 mm diameter quartz tube. The powder was tamped down to provide a smooth sample surface and the ends of the tube were sealed either with epoxy or cotton plugs. The sample tube was then loaded in a sample holder designed to hold these small tubes. Sample luminescence was measured from the front face of the tube, with an angle of 15° between the excitation and emission beams. A 400 nm low-pass filter was used to prevent the primary excitation beam in second or higher order of the emission monochromator from interfering with the results. Excitation and emission spectrometer bandwidths were 1 nm; spectrum step size was 1 nm; integration time was 0.1 second per data point. Data was corrected for the excitation Xe lamp intensity.

Reagents

Except where noted, all reagents were supplied by EMD Chemicals, Inc.

Example 1

Naphthalene-1-carboxylic acid phenylamide

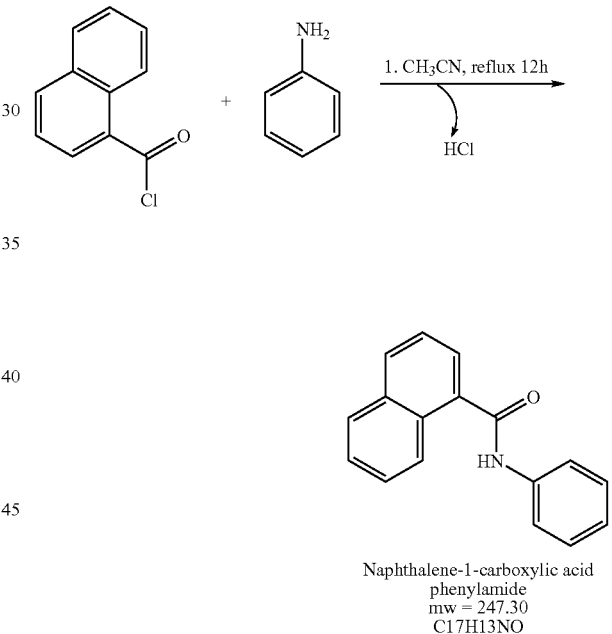

Naphthalene-1-carboxylic acid
phenylamide
mw = 247.30
C17H13NO 4.77 g of 1-naphthoyl chloride (TCI America) was dissolved in 100 ml of anhydrous acetonitrile. To the solution so formed, 2.28 ml of aniline (Sigma-Aldrich) was added in a dropwise fashion over a period of c.a. 20 min. The reaction was then refluxed for 2 h at 82° C. 100 ml of distilled water and 5 ml of concentrated ammonium hydroxide were added along with 100 ml of diethyl ether in a separatory funnel. The phases were separated and the aqueous phase was washed with 100 ml of dichloromethane. The organic fractions were collected and dried with magnesium sulfate, filtered and the solvent was then removed under reduced pressure to yield a white solid 5.07 g (82%; 20.5 mmol).

$^1$H NMR (CD$_3$CN): δ 8.81 (br, 1H), 8.30-8.28 (m, 1H), 8.01 (d, 1H), 7.97-7.95 (m, 1H), 7.77-7.72 (m, 4H), 7.58-7.54 (m, 4H), 7.40 (t, 2H), 7.16 (t, 1H)

$^{13}$C NMR (CD$_3$CN): δ 168.58, 140.01, 135.68, 134.66, 131.44, 131.10, 129.83, 129.32, 128.05, 127.46, 126.47, 126.32, 125.93, 125.17, 121.18, 118.21

Synthesis of Eu[C$_{17}$H$_{13}$NO]$_3$

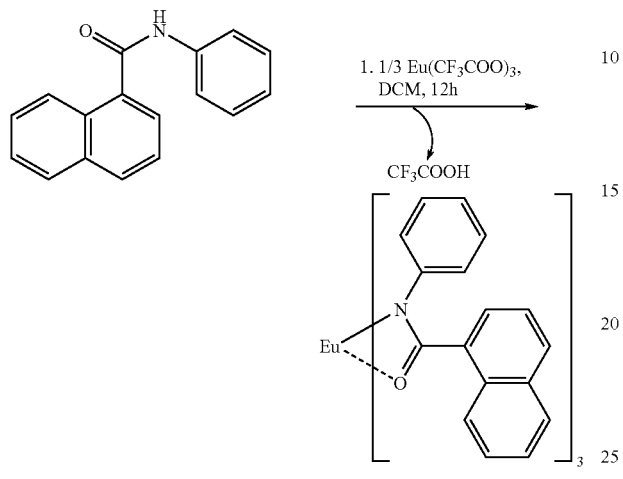

1.47 g of anhydrous europium (III) trifluoroacetate prepared as in Example 1 was combined with 2.22 g of naphthalene-1-carboxylic acid phenylamide in 50 ml of anhydrous dichloromethane. The solution so formed was stirred for 24 h after which the solvent was removed under reduced pressure to yield a white precipitate. The white solid was washed with 20 ml of anhydrous diethyl ether and 10 ml of anhydrous hexane. The white solid was then filtered and dried under vacuum. Yield 64% (1.71 g; 890.84 g/mol).

Elemental Analysis [EuC$_{51}$H$_{39}$N$_3$O$_3$]: calculated. (found) H, 4.40; (4.61), C, 68.53; (68.37), N, 4.70; (4.69)

Synthesis of Eu(C$_{17}$H$_{13}$NO)$_3$(C$_{12}$H$_8$N$_2$)

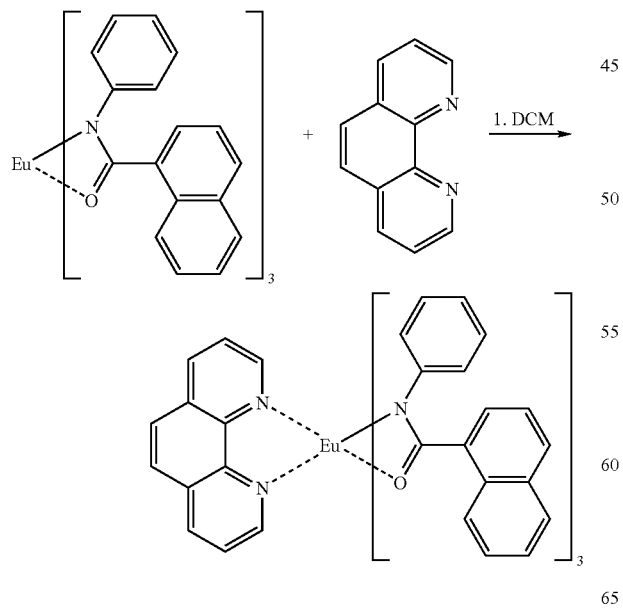

1.50 g of Eu(C$_{17}$H$_{13}$NO)$_3$ was combined with 0.30 g of 1,10-phenanthroline (Sigma-Aldrich) in 25 ml of anhydrous dichloromethane. Upon addition of the latter a white precipitate formed which was found to be insoluble in most common solvents. The white suspension was stirred for 12 h before the precipitate was filtered and washed with 10 ml aliquots of anhydrous dichloromethane and anhydrous tetrahydrofuran before drying the white solid under reduced pressure. Yield 1.32 g (73%).

Elemental Analysis [EuC$_{63}$H$_{47}$N$_5$O$_3$]: calculated (found) H, 4.41; (4.58), C, 70.45; (70.32), N, 6.52; (6.51)

The excitation and luminescence spectra of the product in powder form is shown in FIG. 1.

Example 2

Thiophene-2-carboxilic acid (2-dimethylamino-ethyl)amide

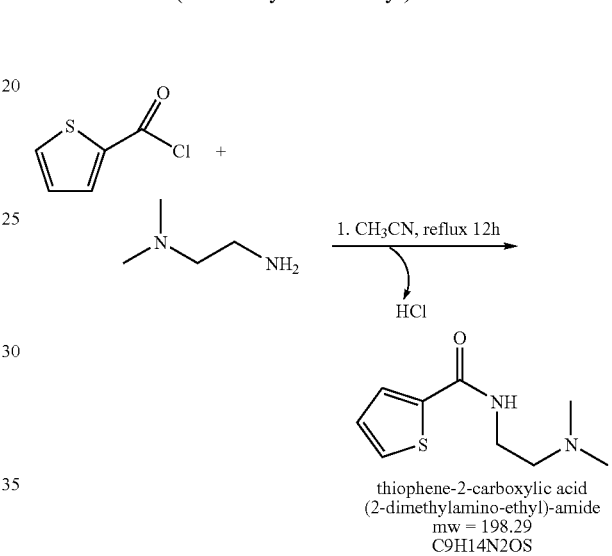

thiophene-2-carboxylic acid
(2-dimethylamino-ethyl)-amide
mw = 198.29
C9H14N2OS 5.31 g of 2-thenoyl chloride (TCI America) was dissolved in 100 ml of anhydrous acetonitrile. 5.51 ml of N,N-dimethylamino-ethane diamine was added in dropwise to the solution so formed. The resulting reaction mixture was stirred for 12 h and then refluxed for 2 h at 82° C. 100 ml of distilled water and 5 ml of concentrated ammonium hydroxide were added along with 100 ml of diethylether in a separatory funnel. The phases were separated and the aqueous phase was washed with 100 ml of dichloromethane. The organic fractions were collected and dried with magnesium sulfate and the solvent was removed under reduced pressure to yield a white solid. Yield 82% (8.12 g; 41.00 mmol)

$^1$H NMR (CD$_3$CN): δ 7.56-7.54 (m, 2H), 7.09-7.07 (m, 2H), 3.39 (q, 2H), 2.43 (t, 2H), 2.19 (s 6H).

$^{13}$C NMR (CD$_3$CN): δ 162.64, 140.97, 131.24, 128.80, 128.61, 59.16, 45.77, 38.47.

Synthesis of Eu(C$_9$H$_{12}$N$_2$OS)$_3$

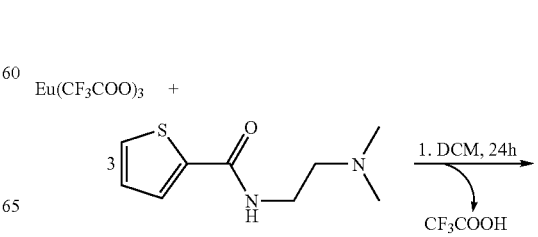

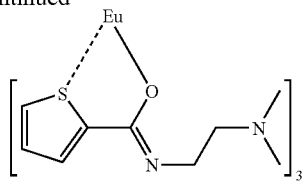

1.473 g of anhydrous europium(III) trifluoroacetate was dissolved in 50 ml of anhydrous dichloromethane. To the solution so formed, 1.785 g of thiophene-2-carboxylic acid (2-dimethylamino-ethyl)-amide was added and the resulting solution was stirred for 24 h. The solvent was removed under reduced pressure and the white solid was washed with anhydrous hexane. The white precipitate was dried to yield 1.84 g (69%; 746.77 g/mol) of final product.

$^1$H NMR (CD$_2$Cl$_2$): δ 7.54 (m, 1H), 7.49 (m, 1H), 7.08 (m, 1H), 3.54 (q, 2H), 2.68 (t, 2H), 2.41 (s, 6H)

$^{13}$C NMR (CD$_2$Cl$_2$): δ 162.2, 130.16, 128.17, 127.99, 58.30, 45.02, 36.88.

Elemental Analysis [EuC$_{27}$H$_{36}$N$_6$O$_3$S$_3$]: calculated. (found) H, 4.89; (4.79), C, 43.77; (42.85), N, 11.34; (11.11)

Synthesis of Eu(C$_9$H$_{12}$N$_2$OS)$_3$(C$_{12}$H$_8$N$_2$)

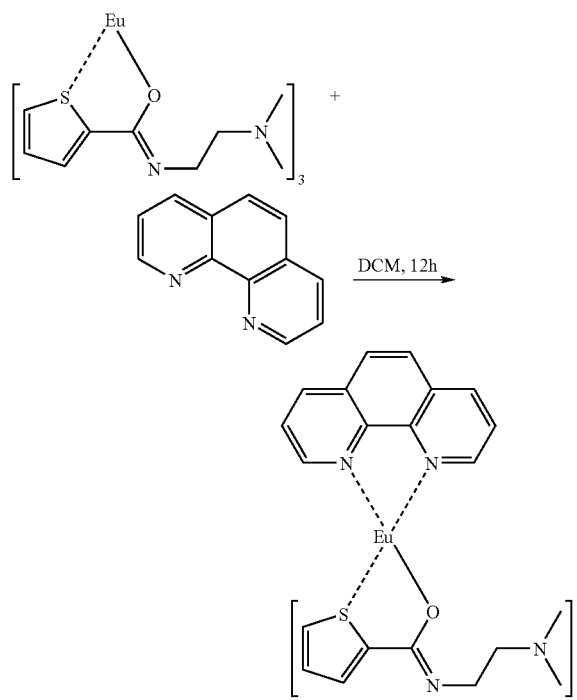

1.50 g of the Eu[C$_9$H$_{13}$N$_2$OS]$_3$ of Example 9 and 0.55 g of 1,10-phenanthroline were dissolved in 25 ml of anhydrous dichloromethane. Upon addition of the latter a white precipitate formed which was found to be insoluble in most common solvents. The white suspension was stirred for 12 h before the precipitate was filtered and washed with anhydrous dichloromethane and anhydrous tetrahydrofuran before drying the white solid under reduced pressure. Yield 1.80 g (88%).

Elemental Analysis [EuC$_{39}$H$_{44}$N$_2$O$_3$S$_3$]: calculated. (found) H, 5.30; (5.41), C, 55.97; (55.90), N, 3.35; (3.34)

Photoluminescence was assessed visually at 10° C. increments until decomposition or extinction of the emitted photoluminescence signal upon excitation of the lanthamide amidate complex with an ultra-violet lamp (Entela model UVL-56; 6 W, 365 nm wavelength).

Example 3

Synthesis of Eu(C$_9$H$_{12}$N$_2$OS)$_3$[OP(C$_6$H$_5$)$_3$]$_2$

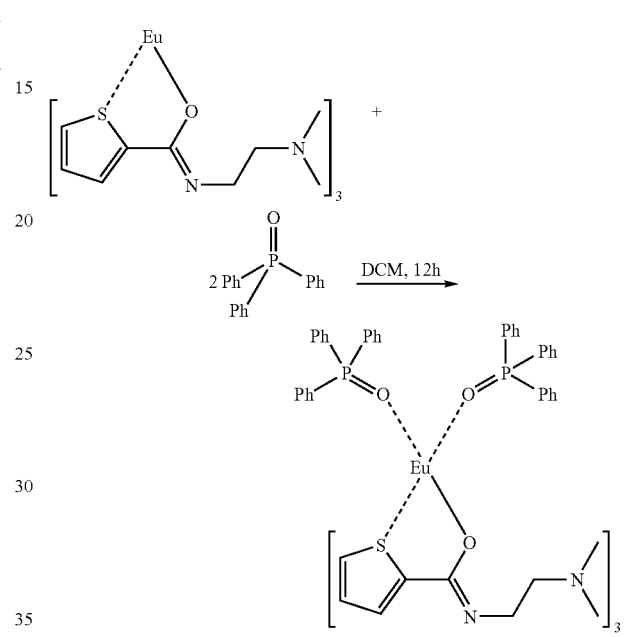

2.24 g (3.0 mmol; 746.77 g/mol) of the Eu[C9H13N2OS]3 of Example 1 was combined with 1.67 g of triphenylphosphine oxide in 25 ml of anhydrous dichloromethane. The solution so formed turned to a clear slightly yellow color upon addition of the triphenylphosphine oxide. The solution was stirred at room temperature for 12 h before removing the solvent under reduced pressure at which point a waxy oil was obtained. The residue was washed with anhydrous hexane and dried under vacuum. Yield 2.85 g (73%).

$^1$H NMR (CD$_2$Cl$_2$): δ 7.62, 7.52, 7.48, 7.44, 7.07, 3.68, 3.64, 2.87, 2.54, 1.81

$^{13}$C NMR (CD$_2$Cl$_2$): δ 139.85, 132.24, 130.34, 128.90, 128.60, 128.04, 68.15, 58.38, 44.84, 25.93.

$^{31}$P NMR (CD$_2$Cl$_2$): δ 27.71

Elemental Analysis [EuC$_{63}$H$_{66}$N$_6$O$_5$S$_3$P$_2$]: calculated. (found) H, 5.13; (5.06), C, 58.32; (57.61), N, 6.48; (6.40)

Photoluminescence was assessed visually at 10° C. increments until decomposition or extinction of the emitted photoluminescence signal upon excitation of the lanthamide amidate complex with an ultra-violet lamp (Entela model UVL-56; 6 W, 365 nm wavelength).

Example 4

Thermal Stability

The thermal stability in the examples below were determined by heating the samples in capillary tubes in a range between 25° C. and 350° C. using a Melt Temp II melting point apparatus from Lab Devices USA. Comparative compositions and data are labeled as compositions purchased from Gelest, Inc. Photoluminescence was assessed visually at 10° C. increments until decomposition or extinction of the emitted photoluminescence signal upon excitation of the lanthamide amidate complex with an ultra-violet lamp (Entela model UVL-56; 6 W, 365 nm wavelength).

Thermal Stability Data

| Lanthanide amidate complex | Decomposition Temperature (Photoluminescence extinction temperature in ° C.) |
|---|---|
| Example 1 | 350 |
| Example 2 | 230 |
| Example 3 | 230 |
| Eu(III) 1,3-diphenyl-1,3-propanedionate (Gelest) | No visible emission after 50 C. |
| Eu(III) thenoyltrifluoroacetate (Gelest) | No visible emission at room temperature |

What is claimed is:

1. A process comprising combining in an organic solvent a lanthanide ester and a compound represented by the formula

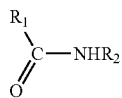

wherein $R_1$ is heteroaryl; $R_2$ is aminoalkyl; resulting in a solution of tris-amidato-lanthanide chelate represented by structure III

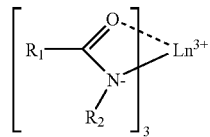

wherein $Ln^{3+}$ designates lanthanide, $R_1$ is heteroaryl; $R_2$ is aminoalkyl; and, addition of a neutrally charged coordinating ligand to the solution of tris-amidato-lanthanide chelate providing a lanthanide chelate represented by structure I or structure II as shown below:

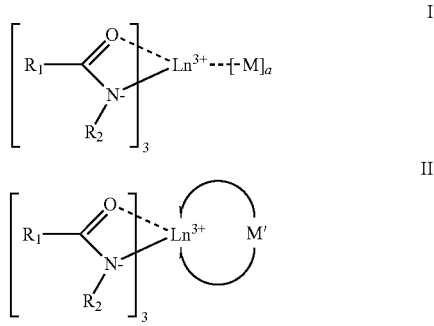

wherein $Ln^{3+}$ designates lanthanide, $R_1$ is heteroaryl; $R_2$ is aminoalkyl; M is tri-phenyl phosphine oxide, M' is 1,10-phenanthroline, a=1 or 2; and the neutrally charged coordinating ligand is tri-phenyl phosphine oxide or 1,10-phenanthroline.

2. The process of claim 1 wherein the lanthanide ester is selected from a lanthanide carboxylate and a lanthanide fluorocarboxylate.

3. The process of claim 2 wherein the lanthanide fluorocarboxylate is selected from $Eu(CF_3COO)_3$, $Dy(CF_3COO)_3$, $Sm(CF_3COO)_3$ and $Tb(CF_3COO)_3$.

4. The process of claim 2 wherein the lanthanide fluorocarboxylate is $Eu(CF_3COO)_3$.

5. The process of claim 1 wherein the solvent is selected from the group consisting of halogenated and non-halogenated linear alkanes, cyclic alkanes and aryl hydrocarbons.

6. The process of claim 1 wherein the solvent is dichloromethane.

7. The process of claim 1 wherein the neutrally charged coordinating ligand is 1,10-phenanthroline.

8. The process of claim 1 wherein Ln is $Eu^{3+}$, $R_1$ is thiophenyl, and $R_2$ is dimethylaminoethyl.

9. The process of claim 1, wherein $R_1$ is thiophenyl, pyridinyl or furanyl.

10. The process of claim 1, wherein $R_2$ is dimethylaminoethyl.

* * * * *